United States Patent

Ogata et al.

Patent Number: 5,478,815
Date of Patent: Dec. 26, 1995

[54] LIVER PROTECTANT TOCOPHERY-ASCORBYL-PHOSPHATE

[75] Inventors: Kazumi Ogata, Toyonaka; Takahiro Sakaue, Itami; Sachiko Matsuura; Rie Nagao, both of Osaka; Shinya Ogino, Itami, all of Japan

[73] Assignee: Senji Pharmaceutical Co., Ltd., Osaka, Japan

[21] Appl. No.: 351,097

[22] Filed: Nov. 30, 1994

[30] Foreign Application Priority Data

Dec. 2, 1993 [JP] Japan .................... 5-302439

[51] Int. Cl.⁶ .................... A61K 31/665; A61K 31/66; A61K 31/355
[52] U.S. Cl. .................... 514/100; 514/120; 514/148; 514/458; 514/893
[58] Field of Search .................... 514/120, 458, 514/100, 148, 893

[56] References Cited

U.S. PATENT DOCUMENTS 4,888,329  12/1989  Ogata et al. .................... 514/100
5,306,713   4/1995  Suetsugu et al. .................... 514/100

*Primary Examiner*—T. J. Criares
*Attorney, Agent, or Firm*—Wenderoth, Lind & Ponack

[57] ABSTRACT

A liver protectant comprising a phosphoric diester compound of the following formula (wherein $R_1$ and $R_2$ are the same or different and each represents hydrogen or methyl) or a pharmacologically acceptable salt thereof.

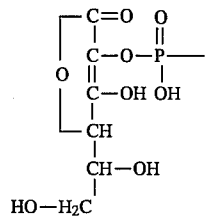

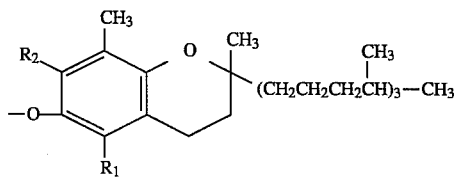

The liver protectant composition of this invention effectively inhibits the elevation of GOT and GPT, among other parameters, so that it is useful for the prevention and therapy, of acute liver disorder, chronic liver disorder and fuminant liver disorder. It can also be used in cirrhosis of the liver with success. The liver protectant composition of this invention can be used with advantage in liver damage associated with alcohol intake and hepatic impairment due to acetaminophen and other drugs. Furthermore, the liver protectant composition of this invention is of value in acute intrahepatic cholestasis.

9 Claims, No Drawings

LIVER PROTECTANT TOCOPHERY-ASCORBYL-PHOSPHATE

FIELD OF THE INVENTION

This invention relates to a useful liver protectant composition. More particularly, this invention relates to a useful liver protectant composition comprising an ascorbyl tocopheryl phosphate compound or a pharmacologically acceptable salt thereof.

BACKGROUND OF THE INVENTION

Many of the liver protectants heretofore in use are compounds having an SH radical, typically cysteine and glutathione. However, while these substances have detoxicating activity on the strength of their active SH radicals, they have the disadvantage that the very SH radicals they have detract from the pharmacological efficacy of concomitant medication.

Therefore, in the field of medicine, a better liver protectant free of the above-mentioned drawback is in demand.

The inventors of this invention who explored the pharmacological action profile of ascorbyl tocophcryl phosphate compounds discovered that these compounds and their pharmacologicalry acceptable salts have a meritorious liver-protective action and, based on this finding, perfected this invention.

SUMMARY OF THE INVENTION

This invention is, therefore, directed to a useful liver protectant composition comprising a phosphoric diester compound of the following formula (wherein $R_1$ and $R_2$ are the same or different and each represents hydrogen or methyl) (hereinafter referred to as the present compound) or a pharmacologically acceptable salt thereof.

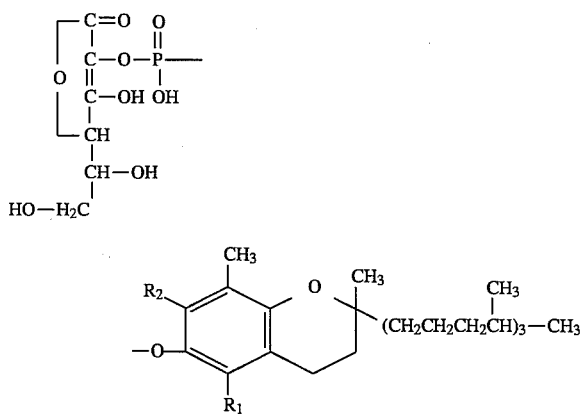

DETAILED DESCRIPTION OF THE INVENTION

The present compound for use in the liver protectant composition of this invention can be synthesized by, for example, the processes described in Japanese Patent Publication H-2-44478 or Japanese Patent Publication H-5-23274, or any improvement thereof.

The compound for use in the liver protectant composition of this invention is already known to be useful as an anticataract agent, a prophylactic and therapeutic agent for climacteric disturbance, a skin care cosmetic ingredient (Japanese Patent Publication H-2-44478), an antiinflammatory agent (Japanese Patent Publication H-1-27044), an antiulcer agent (Japanese Patent Application Kokai S-63-270626) and a prophylactic and therapeutic agent for ischemic organic impairment (Japanese Patent Application Kokai I)-2-111722), among others.

However, it is not yet reported that these compounds are of value as active liver protectants.

The compound for use in the liver protectant composition of this invention may be a free compound or a pharmacologically acceptable salt. Thus, whichever of them can be used for the prevention and the treatment of various liver disorders. The pharmacologically acceptable salt that can be used includes salts with alkali metals such as sodium, potassium, etc. and salts with alkaline earth metals such as calcium and magnesium, among others. Other types of salts, if acceptable from pharmacologic points of view, can also be employed.

According to the clinical objective and need, more than one species of the compound can be incorporated, in an appropriate combination, in the liver protectant composition of this invention.

The compound for use as the active ingredient in the liver protectant composition of this invention is a very safe substance with an extremely low toxic potential and, as such, can be used with advantage for the prophylaxis and treatment of various types of liver disorders. [e.g. the $LD_{50}$ values of L-ascorbyl DL-α-tocopheryl phosphate potassium (abbreviation: EPC-K) $\geq$ 5 g/kg p.o. (rats) and $\geq$ 100 mg/kg i.v. (rats)].

The present compound can be used as an oral or a parenteral liver protectant. The dosage form that can be employed includes such solid preparations as tablets, granules and powders, capsules, etc. and such liquid preparations as injections. These preparations may contain conventional additives such as an excipient, binder, disintegrator, dispersant, reabsorption promoter, buffer, surfactant, solubilizer, preservative, isotonizing agent, stabilizer, pH control agent and so on.

The dosage of the present compound as a liver protectant depends on the species of compound, the patient's body weight and age, indication, dosage form and treatment protocol but may for example be about 1–100 mg/day/adult man in the case of an injectable preparation or about 10–1000 mg/dose/adult man, which is to be administered a few times daily, in the case of an oral preparation.

Unless the object of the invention is compromised, the over protectant composition of this invention may further contain other liver protectant ingredients, such as glycyrrhizln, urusodeoxycholic acid, adenosine triphosphate, etc. and/or other kinds of medicinally active ingredients.

EXAMPLES

The following examples and formulation examples are intended to illustrate this invention in further detail.

Example 1

Effect of the present compound on chronic liver disorder

The effect of the compound on carbon tetrachloride-induced liver disorder was investigated.

1. Experimental animals: Male Fisher rats (body weights about 150 g) (purchased from Charles River Japan).

2. Test substance: L-Ascorbyl DL- α-tocopheryl phosphate potassium (abbreviation: EPC-K).

3. Test method:

Carbon tetrachloride (20% in olive oil), 1 ml/kg, was administered subcutaneously to male Fisher rats twice a week (Tuesdays and Fridays). In parallel but daily, the test substance was administered intraperitoneally in a daily dose of 5 mg/kg. Two months after the start of carbon tetrachloride and test substance dosing, blood was drawn from the lower abdominal aorta under pentobarbital anesthesia and biochemistry tests were performed. As a control drug, physiological saline was used.

4. Results:

The results are shown in Table 1. As seen from Table 1, the present compound significantly inhibited the elevation of GOT and GPT, both of which are indices of liver function, in this rat model of chronic liver disorder constructed using carbon tetrachloride, suggesting that the compound is effective for chronic liver disorder.

TABLE 1

Effect of the present compound on chronic liver disorder

| Group | GOT | GPT |
| --- | --- | --- |
| Control (physiological saline) | 985 ± 695 | 1402 ± 833 |
| EPC-K (5 mg/kg, i.p.) | 230 ± 212*1 | 323 ± 294*1 |
| Normal | 63 ± 7 | 45 ± 4 |

Each value represents mean ± standard deviation (n = 6 – 8).
Significantly different from the control group, *1:P < 0.05.
The GOT and GPT values shown are in units of mU/ml.

Example 2

Effect of the present compound on fulminant liver disorder

The effect of the compound on fulminant liver disorder was investigated.

1. Experimental animals: Male Wistar rats (8 weeks of age) (purchased from Japan SLC).

2. Test substance: EPC-K

3. Test method:

Phenobarbital, 50 mg/2 ml/kg, was administered intraperitoneally to male Wistar rats once daily for 4 days. After an intermission of 24 hours, carbon tetrachloride, 0.64 ml/2 ml (olive oil)/kg, was administered intraperitoneally to induce rat fulminant liver disorder. The test substance was administered intraperitoneally in a dose of 5 mg/kg immediately and 8 hours after induction offulminant liver disorder. Incidentally, the animals were fasted after administration of phenobarbital on day 4. Twenty-four hours after induction of fulminant liver disorder, blood was drawn from the lower abdominal aorta under pentobarbital anesthesis a for biochemistry tests. As a control drug, physiololcical saline was used.

4. Results:

The results are shown in Table 2. As seen from Table 2, the present compound significantly inhibited the elevation of GOT and GPT, both of which are indices of liver function, in the rat model of fulminant liver disorder constructed using carbon tetrachloride and phenobarbital, suggesting that the compound is effective in the treatment of fulminant liver disorder.

TABLE 2

Effect of the present compound on fulminant liver disorder

| Group | GOT | GPT |
| --- | --- | --- |
| Control (physiological saline) | 15221 ± 3359 | 15603 ± 5530 |
| EPC-K (5 mg/kg, i.p.) | 10648 ± 2735*2 | 9695 ± 2671*1 |

Each value represents mean ± standard deviation (n = 8).
Significantly different from the control group, *1: p < 0.05, *2: p < 0.01.
The GOT and GPT values shown are in units of mU/ml.

Example 3

Effect of the present compound on acute liver disorder in rats with vitamin E deficiency The effect of the compound on acute liver disorder was investigated in rats with vitamin E deficiency.

1. Experimental animals: Male Wistar rats (4 weeks of age) (purchased from Clea Japan).

2. Test substance: EPC-K

3. Test method:

Male Wistar rats were maintained on vitamin E-deficient diet for 10 weeks and were then used in the study.

The glutathione (abbreviation: GStI) synthesis inhibitor DL-buthionine sulfoximine (abbreviation: BSO), 1 mmol/kg, was administered intraperitoneally once a day for 3 consecutive days to induce rat liver disorder. Five hours after the last dose of BSO, blood was drawn from the lower abdominal aorta under pentobarbital anesthesia and biochemistry tests were performed.

The test substance was administered orally in a dose of 141 mg/5 ml/kg for one week before induction of the disorder. As a control drug, distilled water was used.

4. Results:

The results are shown in Table 3. As seen from Table 3, the present compound significantly inhibited the elevation of GOT and GPT, both of which are indices of liver function, in rats with vitamin E deficiency, suggesting that the compound is effective for acute liver disorder in rats with vitamin E deficiency.

TABLE 3

Effect of the present compound on liver disorder in rats with vitamin E deficiency

| Group | GOT | GPT |
| --- | --- | --- |
| Control (distilled water) | 380 ± 64 | 53 ± 8 |
| EPC-K (141 mg/kg, p.o.) | 122 ± 36*3 | 16 ± 4*3 |

Each value represents mean ± standard deviation (n = 5).
Significantly different from the control group, *3:p < 0.001.
The GOT and GPT values shown are in units of mU/ml.

Example 4

Effect of the present compound on acute intrahepatic cholestasis

The effect of the compound on acute intrahepatic cholestasis was investigated.

1. Experimental animals: Male Fisher rats (body weights about 150 g) (purchased from Charles River Japan).

2. Test substance: EPC-K

3. Test method:

α-Naphthyl isothiocyanate (abbreviation: ANIT), 100 mg/5 ml (olive oil)/kg, was administered orally to male Fisher rats to induce rat acute intrahepatic cholestasis. The test substance was administered intraperitoneally in a dose of 5 mg/kg immediately and 8 hours after induction of the disorder. Twenty-four hours after induction of acute intrahepatic cholestasis, blood was drawn from the lower abdominal aorta under pentobarbital anesthesia and serum billrubin, GOT and total bile acid were determined. As a control drug, physiological saline was used.

4. Results:

The results are shown in Table 4. As seen from Table 4, the present compound significantly inhibited the elevation of serumbilirubin, GOT and total bile acid, all of which are indices of liver function, suggesting that the compound is remarkably effective for acute intrahepatic cholestasis.

TABLE 4

| Group | Effect of the compound on acute intrahepatic cholestasis | | |
|---|---|---|---|
| | Bilirubin | GOT | Total bile acid |
| Control (physiological saline) | 1.79 ± 0.79 | 366 ± 191 | 550 ± 276 |
| EPC-K (5 mg/kg, i.p.) | 0.33 ± 0.15*2 | 133 ± 81*1 | 53 ± 78*2 |

Each value represents mean ± standard deviation (n = 8).
Significantly different from the control group, *1: $p < 0.05$, *2: $p < 0.01$.
The values are in units of mg/ml for bilirubin, mU/ml for GOT and nmol/ml for total bile acid.

| [Formulation Example 1] Oral tablets | |
|---|---|
| EPC-K | 100 mg |
| Lactose | 75 mg |
| Starch | 20 mg |
| Polyethylene glycol 6000 | 5 mg |

The above ingredients are bldned and compressed into a tablet. If necessary, the tablet may be sugar-coated.

| [Formulation Example 2] Injection | |
|---|---|
| EPC-K | 100 mg |
| Mannitol | 5.0 g |
| 1N-Sodium hydroxide | q.s. |
| Distilled water | to make 100 ml |

The above ingredients are mixed and filtered through a bacterial filter in the routine manner. The filtrate is aseptically filled, in 5 ml portions, into glass ampules, which are closed by fusion, to provide an injection preparation.

The liver protect;ant composition of this invention effectively inhibits the elevation of GOT and GPT, among other parameters, so that it is useful for the prevention and therapy of acute liver disorder, chronic liver disorder and fulminant liver disorder. It can also be used in cirrhosis of the liver with success. The liver protectant composition of this invention can be used with advantage in liver damage associated with alcohol intake and hepatic impairment due to acetaminophen and other drugs. Furthermore, the liver protectant composition of this invention is of value in acute intrahepatic cholestasis.

What is claimed is:

1. A method for the treatment of liver disorder which comprises administering to a patient in need thereof an effective amount of a compound of the formula

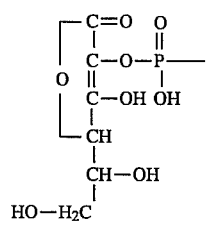

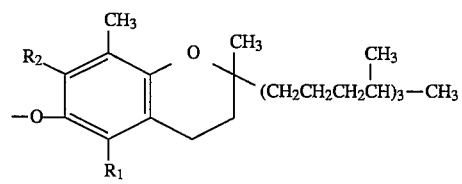

wherein $R_1$ and $R_2$ are the same or different and each represents hydrogen or methyl, or a pharmaceutically acceptable salt thereof.

2. A method for the treatment of liver disorder as claimed in claim 1 wherein both of $R_1$ and $R_2$ represent hydrogen.

3. A method for the treatment of liver disorder as claimed in claim 1 wherein $R_1$ represents hydrogen and $R_2$ represents methyl.

4. A method for the treatment of liver disorder as claimed in claim 1 wherein $R_1$ represents methyl and $R_2$ represents hydrogen.

5. A method for the treatment of liver disorder as claimed in claim 1 wherein both of $R_1$ and $R_2$ represent methyl.

6. A method for the treatment of liver disorder according to claim 1 wherein the disorder to be treated is elevated GOT, GPT, bilirubin or total bile acid.

7. A method for the treatment of liver disorder according to claim 1 wherein the disorder is acute liver disorder or chronic liver disorder.

8. A method for the treatment of liver disorder according to claim 1 wherein the disorder is fulminant hepatitis.

9. A method for the treatment of liver disorder according to claim 1 wherein the disorder is acute intrahepatic cholestasis.

* * * * *